United States Patent
Suzuki et al.

(10) Patent No.: US 7,247,468 B2
(45) Date of Patent: Jul. 24, 2007

(54) METHOD FOR PRODUCING OPTICALLY ACTIVE 1,2-DIOLS BY MICROORGANISM CULTURING

(75) Inventors: Toshio Suzuki, Osaka (JP); Kouji Nishikawa, Osaka (JP); Atsushi Nakagawa, Osaka (JP)

(73) Assignee: Daiso Co., Ltd., Osaka (JP)

( * ) Notice: Subject to any disclaimer, the term of this patent is extended or adjusted under 35 U.S.C. 154(b) by 0 days.

(21) Appl. No.: 11/117,614

(22) Filed: Apr. 29, 2005

(65) Prior Publication Data

US 2006/0019359 A1    Jan. 26, 2006

(30) Foreign Application Priority Data

Apr. 30, 2004  (JP)  ............... 2004-136000

(51) Int. Cl.
 *C12P 41/00* (2006.01)
(52) U.S. Cl. .................................... 435/280
(58) Field of Classification Search .............. None
See application file for complete search history.

(56) References Cited

U.S. PATENT DOCUMENTS

| | | | |
|---|---|---|---|
| 5,212,089 A | | 5/1993 | Suzuki et al. |
| 5,246,843 A | * | 9/1993 | Kasai et al. ............. 435/158 |
| 6,316,233 B2 | * | 11/2001 | Suzuki et al. ............. 435/158 |
| 2002/0132314 A1 | * | 9/2002 | Suzuki et al. ............. 435/158 |
| 2005/0153409 A1 | | 7/2005 | Nishikawa et al. |

FOREIGN PATENT DOCUMENTS

| | | |
|---|---|---|
| JP | 3 191794 | 8/1991 |
| JP | 3 191795 | 8/1991 |
| JP | 6 30790 | 2/1994 |
| JP | 1994-30790 | 2/1994 |
| JP | 6 209781 | 8/1994 |
| JP | 1994-209781 | 8/1994 |
| JP | 11 46758 | 2/1999 |
| JP | 11 221092 | 8/1999 |
| JP | 2001-149090 | 6/2001 |
| JP | 2002 253295 | 9/2002 |
| WO | WO 98/29558 | 7/1998 |

\* cited by examiner

*Primary Examiner*—Sandra E. Saucier
(74) *Attorney, Agent, or Firm*—Westerman, Hattori, Daniels & Adrian, LLP.

(57) ABSTRACT

A method for producing an optically active compound comprising:

a first step of culturing a microorganism capable of assimilating either the R-isomer or the S-isomer of a compound represented by Formula (1):

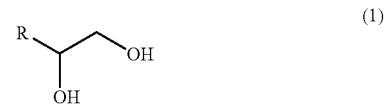

wherein R is a methyl, ethyl, propyl, chloromethyl, or hydroxyethyl group, in a culture medium whose $Ca^{2+}$ concentration at the beginning of culturing is controlled and which contains a racemic mixture of the compound as a carbon source; and a second step of recovering the optically active compound remaining in the culture broth.

10 Claims, No Drawings

METHOD FOR PRODUCING OPTICALLY ACTIVE 1,2-DIOLS BY MICROORGANISM CULTURING

BACKGROUND OF THE INVENTION

1. Field of the Invention

The present invention relates to a method for producing optically active 1,2-diols, including optically active halogenohydrins, that can be used as chiral building blocks in the synthesis of optically active compounds used as pharmaceuticals, agrichemicals, physiologically active substances, and the like, and intermediates therefor. In particular, the present invention relates to a method for producing optically active 1,2-diols by means of assimilative optical resolution.

2. Description of the Related Art

Known biological methods for producing optically active 1,2-diols, including optically active halogenohydrins, using microorganisms are a method for producing an optically active 1,2-propanediol as disclosed in Japanese Unexamined Patent Publication No. 1994-30790 and a method for producing (S)-3-halogeno-1,2-propanediols as disclosed in Japanese Unexamined Patent Publication No. 1994-209781. In both methods, microorganisms as a resting cells belonging to the genus *Pseudomonas* are used.

The inventors have previously disclosed a method for producing an optically active 1,2-propanediol in Japanese Unexamined Patent Publication No. 2002-253295 and methods for producing optically active 3-chloro-1,2-propanediol in Japanese Unexamined Patent Publication Nos. 1991-191795, 2001-149090, and 1991-191794, in which a microorganism that proliferates by digesting an optically active compound as a carbon source is cultured in a culture medium containing a racemic mixture thereof as a sole carbon source, and the optically active compound that remains after culturing is recovered (assimilative optical resolution).

It is now known that, in the assimilative optical resolution described in the aforementioned patent publications, the ability of microorganisms to select optically active compounds is greatly affected by the quality and batch of the culture medium, especially the quality of water used in preparing the culture medium.

Generally, calcium is one of the important mineral elements in living bodies, and $Ca^{2+}$ is known to be involved in controlling many life phenomena. There are industrially applicable techniques for microorganism culturing that take the $Ca^{2+}$ concentration into consideration, for example, culturing for the production of unsaturated aliphatic acids (WO 98/029558), culturing for the decomposition of trichloroethylene (Japanese Unexamined Patent Publication No. 1999-46758), and culturing for the production of erythritol (Japanese Unexamined Patent Publication No. 1999-221092). However, there has been no report of the relationship between $Ca^{2+}$ concentration and ability to select an optically active compound, i.e., the relationship between $Ca^{2+}$ concentration and reaction rate and stereoselectivity (yield of chiral compound).

BRIEF SUMMARY OF THE INVENTION

An object of the invention is to provide a method for producing an optically active compound which is applicable to producing optically active 1,2-diols with a high optical purity in a shorter period of time and in a higher yield.

The inventors conducted extensive research to achieve the object described above, and found that, in producing an optically active 1,2-diol according to assimilative optical resolution using a microorganism, the rate of optical resolution and the yield of optically active compound can be significantly enhanced by controlling the $Ca^{2+}$ concentration of the culture medium at the beginning of culturing within a specific range. The inventors accomplished the present invention based on this finding.

The present invention has been accomplished based on the finding described above and provides methods for producing optically active substances as presented below:

Item 1. A method for producing an optically active compound comprising:

a first step of culturing a microorganism capable of assimilating either the R-isomer or the S-isomer of a compound represented by Formula (1):

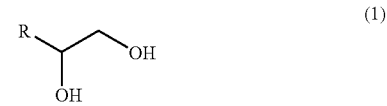

wherein R is a methyl, ethyl, propyl, chloromethyl, or hydroxyethyl group, in a culture medium whose $Ca^{2+}$ concentration at the beginning of culturing is controlled and which contains a racemic mixture of the compound as a carbon source; and a second step of recovering the optically active compound remaining in the culture broth.

Item 2. The production method according to item 1, wherein in the first step the $Ca^{2+}$ concentration of the culture medium at the beginning of culturing is controlled such that the optically active compound represented by Formula (1) remaining in the culture broth acquires an optical purity of 98% e.e. within 130 hours.

Item 3. The production method according to item 1, wherein the microorganism belongs to the genus *Pseudomonas*.

Item 4. The production method according to item 1, wherein the $Ca^{2+}$ concentration of the culture medium at the beginning of culturing is 3 to 40 ppm.

Item 5. The production method according to item 1, wherein the compound represented by Formula (1) is 1,2-propanediol, the $Ca^{2+}$ concentration of the culture medium at the beginning of culturing in the first step is 3 to 13 ppm, and (R)-1,2-propanediol is recovered in the second step.

Item 6. The production method according to item 5, wherein the microorganism is *Pseudomonas nitroreducens* DS-S-RP8 (International Deposition No. FERM BP-7793).

Item 7. The production method according to item 1, wherein the compound represented by Formula (1) is 3-chloro-1,2-propanediol, the $Ca^{2+}$ concentration of the culture medium at the beginning of culturing in the first step is 3 to 40 ppm, and (S)-3-chloro-1,2-propanediol is recovered in the second step.

Item 8. The production method according to item 7, wherein the microorganism is *Pseudomonas* sp. DS-SI-5 (International Deposition No. FERM BP-7080).

Item 9. The production method according to item 1, wherein the compound represented by Formula (1) is 3-chloro-1,2-propanediol, the $Ca^{2+}$ concentration of the culture medium at the beginning of culturing in the first step is 5 to 28 ppm, and (R)-3-chloro-1,2-propanediol is recovered in the second step.

Item 10. The production method according to item 9, wherein the microorganism is *Pseudomonas* sp. DS-K-2D1 (International Deposition No. FERM BP-3096).

The method of the present invention enables a stable and enhanced production of optically active 1,2-diols, including optically active halogenohydrins, in large amounts. In particular, when optically active 1,2-diols, including optically active halogenohydrins, are produced according to an assimilative optical resolution reaction, optically active compounds having a high optical purity of 98% e.e. or greater can be obtained in a high yield in a short period of time. Moreover, the inventors have succeeded in attaining this stable and enhanced production without much fluctuation among production batches in the yield of optically active compound and the rate of optical resolution.

DETAILED DESCRIPTION OF THE INVENTION

Hereinbelow, the present invention is described in more detail.

The method for producing an optically active compound of the present invention comprises a first step of culturing a microorganism capable of assimilating either the R-isomer or the S-isomer of a compound represented by Formula (1):

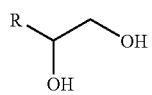

(1)

wherein R is a methyl, ethyl, propyl, chloromethyl, or hydroxyethyl group, in a culture medium comprising a racemic mixture of the compound as a carbon source; and a second step of recovering the remaining optically active compound from the resulting culture broth. In particular, the method of the present invention is for producing the S-isomer or the R-isomer of a compound represented by Formula (1) by means of assimilative optical resolution using a microorganism. In the present invention, the culture medium at the beginning of culturing in the first step has a controlled $Ca^{2+}$ concentration. The $Ca^{2+}$ concentration may be controlled such that the optical purity of the compound represented by Formula (1) remaining in the culture broth becomes 98% e.e. within 130 hours.

The following techniques are usable in the present invention: batch culturing in which an entire substrate is supplied at once, fed-batch culturing in which a substrate is supplied in portions, and continuous culturing in which a culture medium containing a substrate is continuously supplied and the resulting product is continuously discharged. The "time" to reach 98% e.e. refers to the culturing time with respect to batch culturing and fed-batch culturing, and the retention time with respect to continuous culturing. With respect to continuous culturing, "the $Ca^{2+}$ concentration of a culture medium at the beginning of culturing" refers to the $Ca^{2+}$ concentration in the fermentor at the beginning of continuous culturing. Furthermore, it is preferable to control the $Ca^{2+}$ concentration of culture media supplied during culturing. For example, the $Ca^{2+}$ concentration of culture media to be supplied may be controlled to be within the maximum allowable concentration of $Ca^{2+}$ at the beginning of culturing such that the retention time to reach 98% e.e. is no more than 130 hours.

Starting Compounds

A racemic mixture of a compound represented by the aforementioned Formula (1) is used as a starting material of the production of an optically active compound by assimilative optical resolution. In particular, racemic mixtures of compounds selected from the group consisting of 1,2-propanediol, 1,2-butanediol, 1,2-pentanediol, 3-chloro-1,2-propanediol, and 1,2,4-butanediol are used.

These compounds can be produced by, for example, the hydrolysis of the corresponding epoxides under acidic conditions created by sulfuric acid. Methods for producing diols from epoxides are described in, for example, *Tetrahedr. Asymm*, (1994) Vol. 5, No. 2, 239-246 and *Bull. Soc. Chim*, (1926) Vol. 39, 699-700.

Microorganisms

Microorganisms usable in the method of the present invention are those capable of selectively assimilating either the S-isomer or the R-isomer of a compound represented by Formula (1). One kind of microorganism may be used, or two or more kinds of microorganisms may be use in combination insofar as they can assimilate the target optically active isomer in a starting racemic mixture.

Examples of microorganisms that can efficiently assimilate one optically active isomer of a compound of Formula (1) are those that belong to the genus *Pseudomonas*. In particular, *Pseudomonas nitroreducens* DS-S-RP8 (International Deposition No. BP-7793), *Pseudomonas* sp. DS-SI-5 (International Deposition No. FERM BP-7080), and *Pseudomonas* sp. DS-K-2D1 (International Deposition No. FERM BP-3096) are examples of preferable strains.

*Pseudomonas nitroreducens* DS-S-RP8 is a strain that selectively assimilates (S)-1,2-propanediol in an efficient manner. *Pseudomonas* sp. DS-SI-5 is a strain that selectively assimilates (R)-3-chloro-1,2-propanediol in an efficient manner. *Pseudomonas* sp. DS-K-2D1 is a strain that selectively assimilates (S)-3-chloro-1,2-propanediol in an efficient manner.

*Pseudomonas* sp. DS-SI-5, International Deposition No. FERM BP-7080, was deposited at the National Institute of Bio-Science and Human-Technology. Agency of Industrial Science and Technology, 1-3, Higashi 1-chome. Tsukuba-shi. Ibaraki-ken. 305-8566 Japan. on Oct. 7, 1999, and accepted as established under the Budapest Treaty on the International Recognition of the Deposit of Microorganisms for the Purposes of Patent Procedure;

*Pseudomonas nitroreducens* DS-S-RP8, International Deposition No. FERM BP-7793, was deposited at the International Patent Organism Depository, National Institute of Advanced Industrial Science and Technology of AIST Tsukuba Central 6, 1-1, Higashi 1-chome, Tsukubashi. Ibaraki-ken, 305-8566 Japan, on Jun. 29, 2001, and accepted as established under the Budapest Treaty on the International Recognition of the Deposit of Microorganisms for the Purposes of Patent Procedure:

*Pseudomonas* sp. DS-K-2D1, International Deposition No. FERM BP-3096, was deposited at the Fermentation Research Institute, Agency of Industrial Science and Technology. 1-3, Higashi 1-chome. Tsukuba-shi. Ibaraki-ken, 305-8566 Japan on Nov. 15, 1989 (as FERM P-11110 and, thereafter, its control was transferred in the Fermentation Research Institute on Sep. 12, 1990 and accepted as established under the Budapest Treaty on the International Recognition of the Deposit of Microorganisms for the Purposes of Patent Procedure:

Likewise, for 1,2-butanediol, 1,2-pentanediol, and 1,2,4-butanetriol, productivity for the optically active compounds can be enhanced by using microorganisms that can specifically assimilate one of these optically active compounds and a culture medium having a controlled $Ca^{2+}$ concentration at the beginning of culturing.

Culturing Conditions

Culture media in which the aforementioned microorganisms are cultured for seed culturing are not limited insofar as the microorganisms can proliferate. For example, common nutrient media for microorganism culturing containing peptone, yeast extract, glycerol, etc., can be used. It is necessary to quantify in advance the $Ca^{2+}$ in the culture medium for assimilative optical resolution that is derived from the seed culture so as to help control the $Ca^{2+}$ concentration of the culture medium to be within the aforementioned optimum range.

Culture media usable for assimilative optical resolution are not limited insofar as the $Ca^{2+}$ concentration thereof at the beginning of culturing can be controlled within the aforementioned range. The use of minimal media as described below allows the $Ca^{2+}$ concentration to be easily controlled.

Water-soluble salts that generate $Ca^{2+}$ can be used as $Ca^{2+}$ sources without limitation. Calcium chloride is preferably used. It is preferable to use ion-exchanged water to prepare culture media, thereby obviating the consideration of any $Ca^{2+}$ in the water.

To ensure the time for the remaining optically active compound of Formula (1) to reach an optical purity of 98% e.e. is within 130 hours, the $Ca^{2+}$ concentration of a culture medium is usually controlled to be about 3 to about 40 ppm, although this varies depending on the bacterial strains, starting compounds, culturing conditions, and other factors.

For example, when *Pseudomonas nitroreducens* DS-S-RP8 is used to obtain (R)-1,2-propanediol by optically resolving by assimilation a racemic mixture of 1,2-propanediol, the $Ca^{2+}$ concentration at the beginning of culturing is preferably about 3 to about 13 ppm, and more preferably about 9 to about 12 ppm.

When *Pseudomonas* sp. DS-SI-5 is used to obtain (S)-3-chloro-1,2-propanediol by optically resolving by assimilation a racemic mixture of 3-chloro-1,2-propanediol, the $Ca^{2+}$ concentration of a culture medium at the beginning of culturing is preferably about 3 to about 40 ppm, and more preferably about 7 to about 37 ppm.

When *Pseudomonas* sp. DS-K-2D1 is used to obtain (R)-3-chloro-1,2-propanediol by optically resolving by assimilation a racemic mixture of 3-chloro-1,2-propanediol, the $Ca^{2+}$ concentration of a culture medium at the beginning of culturing is preferably about 5 to about 28 ppm, and more preferably about 9 to about 27 ppm.

When the $Ca^{2+}$ concentration is within the aforementioned ranges, the desired optically active compounds having an optical purity of 98% e.e. or greater can be obtained in a short period of time and in a high yield.

The $Ca^{2+}$ concentrations herein are represented by values measured by the ICP atomic emission spectrometry.

A racemic mixture of a compound represented by Formula (1) above (hereinafter sometimes referred to as the "substrate"), which is the target of resolution, is used as a carbon source. To efficiently conduct optical resolution, the substrate is preferably used as the sole carbon source.

As described above, in the present invention, batch culturing in which the entire substrate is supplied at once at the beginning of culturing may be used as well as fed-batch culturing in which the substrate is supplied in portions. In fed-batch culturing, the substrate may be introduced continuously or intermittently according to the frequency of substrate introduction and the amount thereof, determined based on, for example, the quantity of acid or alkali used to titrate the change in pH that occurs as the reaction progresses, or the concentration of substrate (carbon source) in the reaction solution (Kasai et al., Seibutsu-kogaku kaishi, 1997, 75, 255-275).

Moreover, continuous culturing can be used in the present invention. An example of continuous culturing is, as with fed-batch culturing, supplying a culture medium containing the substrate continuously according to the amount of the substrate to be added determined based on the quantity of acid or alkali used to titrate the change in pH that occurs as the reaction progresses, or the concentration of substrate (carbon source) in a reaction solution; and then collecting continuously-discharged culture fluid containing the optically active compound (Japanese Unexamined Patent Publication No. 2004-041076).

An excessively high substrate (carbon source) concentration in a culture medium sometimes inhibits microorganism growth. In other words, substrates have a growth inhibition concentration toward microorganisms. Assimilative optical resolution is a reaction that occurs as a microorganism grows. It is thus necessary to keep the concentration of substrate in a culture medium during culturing lower than the growth inhibition concentration. Since substrate is introduced more than once in fed-batch culturing and continuous culturing, the total amount of substrate introduced can be greater than in batch culturing while still keeping the concentration of substrate in the culture medium during culturing lower than the growth inhibition concentration.

In batch culturing, the concentration of substrate at the beginning of culturing is controlled to be preferably about 0.1 to about 15 w/v %, and more preferably about 1 to about 5 w/v %. When the concentration is within the aforementioned ranges, optical resolution efficiently progresses without substrate or optically active compound hindering the growth of a microorganism.

In fed-batch culturing and continuous culturing, the total amount of substrate introduced is controlled to be preferably about 0.1 to about 15 w/v %, and more preferably about 1 to about 10 w/v %, based on the culture medium. Furthermore, the concentration of substrate during culturing is controlled to be preferably about 1 to about 7 w/v %, and more preferably about 1 to about 5 w/v %. When the concentration is within the aforementioned ranges, optical resolution efficiently progresses without substrate or optically active compound hindering microorganism growth. In fed-batch culturing, substrate may be introduced several times while substrate may be introduced as and when necessary as the reaction progresses, to control the concentration of substrate during culturing within the aforementioned ranges. The extent of the reaction can be determined by, for example, pH, substrate concentration, turbidity created by the microorganism, amount of carbon dioxide produced, etc.

Components other than the carbon source are not limited. Those that are usually used in microorganism culturing are usable. For example, ammonium sulfate, ammonium nitrate, ammonium phosphate, and like inorganic ammonium salts are usable as nitrogen sources. Phosphates, magnesium salts, potassium salts, manganese salts, iron salts, zinc salts, copper salts, and like inorganic salts may be used to enable assimilative optical resolution to progress efficiently. Furthermore, various antifoaming agents can be used as necessary.

The pH of the culture medium during culturing may be controlled to be about 4 to about 10, and preferably about 5 to about 9. Usually, the pH is controlled to be about the optimal pH of a microorganism for use insofar as it is within the aforementioned ranges. As the assimilative optical resolution progresses, if the pH of a culture medium gradually increases or decreases, a suitable alkali source or acid source may be added to the culture medium to control the pH thereof to be about the optimal pH. The amount of acid source or alkali source to be added is proportional to the extent of assimilative optical resolution. Therefore, when fed-batch culturing is selected, the amount of substrate supplied can be determined using the amount of acid source or alkali source as an index. Examples of alkali sources are aqueous sodium carbonate solutions, aqueous potassium carbonate solutions, aqueous ammonium carbonate solutions, and like aqueous alkali carbonate solutions; aqueous sodium hydroxide solutions, aqueous potassium hydroxide solutions, and like aqueous alkali metal hydroxide solutions; aqueous ammonia solutions; etc. Acid sources include hydrochloric acid, phosphoric acid, and like commonly used acids. It is preferable not to use calcium salts so as to avoid affecting the $Ca^{2+}$ concentration of the culture medium.

The culturing temperature is usually about 15 to about 40° C., and preferably about 20 to about 37° C. Usually, the temperature is controlled to be about the optimal temperature of the microorganism used, for example, about 30° C., insofar as it is within the aforementioned ranges. Culturing is usually conducted aerobically, although this depends on the microorganism selected.

Although culturing is usually continued until the optical purity of the desired optically active compound reaches 98% e.e. or greater, the reaction may be terminated before the optically active compound attains the aforementioned optical purity depending on the application therefor. Usually, about 24 to about 130 hours of culturing yields an optically active compound having an optical purity of 98% e.e. or greater although the time varies depending on the type and concentration of substrate, microorganism, culturing conditions, etc. An excessively long period of culturing does not contribute to the growth of microorganisms, and hence does not help assimilative optical resolution to progress. Moreover, it is preferable to terminate the reaction within the aforementioned period of time for economical production. It is preferable to determine the end point of the reaction by monitoring the change in pH of the culture medium as the reaction progresses, measuring the amount of the desired optically active compound produced (the amount of it remaining) by gas chromatography, or by using similar techniques.

Recovery of Optically Active Compound

Optically active compound remaining in a culture fluid obtained in such a manner can be recovered according to standard methods. For example, the microorganism can be removed from the culture fluid by filter pressing, ultrafiltration, centrifugation, etc., and the supernatant can then be concentrated by an evaporator and extracted with ethyl acetate, diethyl ether, or like solvents. Thereafter, the extract is dried using anhydrous magnesium sulfate or the like, and the solvent is removed under reduced pressure, thereby giving the optically active compound as a syrup. Furthermore, this optically active compound can be purified according to standard techniques such as distillation and chromatography.

EXAMPLES

Examples are given below to illustrate the invention in more detail, but the scope of the invention is not limited to these Examples. In the Examples, "%" refers to "v/v %" unless otherwise specified.

Strains

*Pseudomonas nitroreducens* DS-S-RP8 (International Deposition No. FERM BP-7793), *Pseudomonas* sp. DS-SI-5 (International Deposition No. FERM BP-7080), and *Pseudomonas* sp. DS-K-2D1 (International Deposition No. FERM BP-3096) used in the Examples below have been deposited at the International Patent Organism Depositary of the National Institute of Advanced Industrial Science and Technology.

Method for Measuring $Ca^{2+}$ Concentration $Ca^{2+}$ concentrations were measured by the ICP atomic emission spectrometry using an ICP atomic emission spectrometer (manufactured by Nippon Jarrell Ash, ICAP-575 Mark II). Device settings: an output of 1.2 kw and a torch of +1.0 cm. One measurement refers to the integration of the results of three detections of short wavelengths for 3 seconds, main wavelengths for 3 seconds, and long wavelengths for 3 seconds.

Example 1

Production of (R)-1,2-propanediol

A 500 ml Erlenmeyer flask equipped with baffles and accommodating 100 ml of a nutrient culture medium containing 2% yeast extract and 1% glycerol (pH 7.2) in ion-exchanged water was autoclaved at 121° C. for 15 minutes. In this flask was inoculated a small amount of *Pseudomonas nitroreducens* DS-S-RP8 that had been cultured on an agar nutrient culture medium of the same nutrient composition, and cultured at 30° C. for 24 hours, thereby giving a seed culture.

TABLE 1

| Component of culture medium | Concentration |
| --- | --- |
| Ammonium sulfate | 1% |
| Disodium hydrogen phosphate | 0.02% |
| Dipotassium hydrogen phosphate | 0.02% |
| Monosodium dihydrogen phosphate | 0.04% |
| Magnesium sulfate | 0.05% |
| Ferrous sulfate heptahydrate | 10 ppm |
| Copper sulfate pentahydrate | 1 ppm |
| Manganese nitrate | 1 ppm |

Ion-exchanged water was used to prepare 2.1 l of an aqueous solution containing inorganic components as shown in Table 1 above. The $Ca^{2+}$ concentration thereof was adjusted using calcium chloride. This aqueous solution was introduced into a 5 l fermentor, mixed with 100 g of racemic 1,2-propanediol, and autoclaved at 121° C. for 15 minutes, thereby giving a minimal culture medium that contains racemic 1,2-propanediol as a sole carbon source. In this manner, 4 different minimal culture media were prepared having $Ca^{2+}$ concentrations at the beginning of culturing of 3, 9, 12, or 15 ppm. With respect to these minimal culture media, the $Ca^{2+}$ concentration derived from the seed culture was 1 ppm.

The minimal culture was combined with 100 ml of the aforementioned seed culture to conduct a reaction (culturing) at 30° C. and 500 rpm with a ventilation volume of 0.25 l /min for 72 to 120 hours. The pH of the culture medium was measured and controlled by a pH controller using a 25%

(w/w) aqueous sodium hydroxide solution so as to maintain the pH at 6.9. Racemic 1,2-propanediol was gradually introduced as the reaction progressed in order to prevent the concentration thereof in the culture from exceeding 5%, which is the threshold of the growth inhibition concentration of the aforementioned microorganism. A total 200 g of the racemic mixture was added. The reaction was terminated when the optical purity of the remaining (R)-1,2-propanediol measured by gas chromatographic analysis reached 99.0% e.e. or greater.

Table 2 below shows the relationship between $Ca^{2+}$ concentration and reaction time and between $Ca^{2+}$ concentration and yield. Yield refers to the proportion of the remaining optically active compound relative to the initial concentration of the substrate (carbon source). It is clear from Table 2 that when the $Ca^{2+}$ concentration was from 3 to 12 ppm, the optical purity of the remaining (R)-1,2-propanediol exceeded 99% e.e. A $Ca^{2+}$ concentration of 9 ppm resulted in a particularly short reaction time. A $Ca^{2+}$ concentration of 3 ppm resulted in assimilative optical resolution proceeding slowly with the yield, i.e., stereoselectivity, being a little low, but still being practically usable. When the $Ca^{2+}$ concentration was 15 ppm, assimilative optical resolution was inhibited, and the optical purity therefore did not reach 98% e.e.

TABLE 2

| $Ca^{2+}$ concentration (ppm) | Reaction time (hours) | Optical purity (% e.e.) | Yield of R-isomer (>99% e.e.) |
|---|---|---|---|
| 3 | 110 | >99 | 28 |
| 9 | 72 | >99 | 40 |
| 12 | 80 | >99 | 37 |
| 15 | Did not complete | 43 | NA* |

NA*: Not Applicable

After culturing, the microorganism was removed by centrifugation, and the supernatant was concentrated using an evaporator and extracted with diethyl ether. The extract was then dried over anhydrous magnesium sulfate, and the solvent was removed under reduced pressure, thereby giving 1,2-propanediol as a syrup.

This 1,2-propanediol was trifluorinated in dichloromethane using anhydrous trifluoroacetic acid, and the optical purity thereof was measured by gas chromatography using a capillary column G-TA (0.25 mm (ID)×30 m (L)) manufactured by Astech Corporation under following conditions:

Column temperature: 60° C.

Detector temperature: 200° C.

Carrier gas: nitrogen

Flow rate: 0.5 ml/min

Detector: FID

Split ratio: 200/1

Retention time of 1,2-propanediol: 11.4 minutes for (R)-1,2-propanediol and 17.6 minutes for (S)-1,2-propanediol.

Example 2

Production of (S)-3-Chloro-1,2-Propanediol

The microorganism used herein was *Pseudomonas* sp. DS-SI-5. Seed cultures were prepared in the same manner as in Example 1 except that a culture medium containing 1% peptone, 1% yeast extract and 1% glycerol, or a culture medium containing 2% yeast extract and 1% glycerol were used.

Thereafter, 6 minimal culture media were prepared in the same manner as in Example 1 except that 63 g of racemic 3-chloro-1,2-propanediol was used, and the $Ca^{2+}$ concentrations of the culture media at the beginning of culturing (after inoculating the seed cultures) was adjusted to be 7, 20, 25, 30, 37, or 43 ppm. In the $Ca^{2+}$ concentration of these minimal culture media at the beginning of culturing, 3 or 7 ppm was derived from the seed cultures.

Each minimal culture medium was combined with 100 ml of an aforementioned seed culture to conduct a reaction (culturing) at 30° C. and 510 rpm with a ventilation volume of 0.25 l/min for 70 hours. The pH of the culture media was measured and controlled by a pH controller. The pH decrease due to the dechlorination reaction was titrated using a 25% (w/w) aqueous sodium hydroxide solution so as to maintain the pH at 6.9.

Racemic 3-chloro-1,2-propanediol was continuously supplied using the pH controller in an amount 1.8 times as much as the molar amount of sodium hydroxide added according to the titration. The supply of racemic 3-chloro-1,2-propanediol was terminated when the total amount thereof reached 200 g, except that when the $Ca^{2+}$ concentration at the beginning of culturing was 43 ppm, the total amount of racemic 3-chloro-1,2-propanediol supplied was 148 g (Kasai et al., Seibutsu-kogaku kaishi, 1997, 75, 255-275). The concentration of racemic 3-chloro-1,2-propanediol during culturing did not exceed 5%, which is the threshold of the growth inhibition concentration of the aforementioned microorganism. The reaction was terminated when the optical purity of the remaining (S)-3-chloro-1,2-propanediol measured by gas chromatographic analysis reached 99.0% e.e. or greater.

Table 3 below shows the relationship between $Ca^{2+}$ concentration and reaction time and between $Ca^{2+}$ concentration and yield. It is clear from Table 3 that when the $Ca^{2+}$ concentration was from 7 to 37 ppm, the optical purity of the remaining (S)-3-chloro-1,2-propanediol exceeded 99% e.e. The $Ca^{2+}$ concentration of 37 ppm resulted in a particularly short reaction time. However, when the $Ca^{2+}$ concentration was 43 ppm, only 148 g of the racemic mixture substrate (carbon source) could be supplied due to the reduced activity of the microorganism, and the optical purity did not reach 98% e.e. or greater due to deactivation of the microorganism during culturing.

TABLE 3

| $Ca^{2+}$ concentration* (ppm) | Reaction time (hours) | Optical purity (% e.e.) | Yield of S-isomer (>99% e.e.) |
|---|---|---|---|
| 7(7) | 57 | >99 | 50 |
| 20(7) | 46 | >99 | 50 |
| 25(3) | 47 | >99 | 50 |
| 30(3) | 43 | >99 | 50 |
| 37(3) | 38 | >99 | 50 |
| 43(3) | Did not complete | 60 | NA** |

*Values in parentheses refer to $Ca^{2+}$ concentrations derived from seed cultures
**Not Applicable After culturing, the microorganism was removed by centrifugation, and the supernatant was concentrated using an evaporator and extracted with diethyl ether. The extract was then dried over anhydrous magnesium sulfate, and the solvent was removed under reduced pressure, thereby giving 3-chloro-1,2-propanediol as a syrup.

This 3-chloro-1,2-propanediol was dissolved in 2-propanol and converted into glycidol by addition of 12.5 N sodium hydroxide solution, and the optical purity thereof was measured by gas chromatography using a capillary column A-PH (0.25 mm (ID)×30 m (L)) manufactured by Astech Corporation under following conditions:
Column temperature: 45° C.
Detector temperature: 200° C.
Carrier gas: helium
Flow rate: 0.5 ml/min
Detector: FID
Split ratio: 100/1
Retention time of glycidol: 33.8 minutes for (R)-3-chloro-1,2-propanediol isomer and 35.2 minutes for (S)-3-chloro-1,2-propanediol isomer.

Example 3

Production of (R)-3-Chloro-1,2-Propanediol

The microorganism used herein was *Pseudomonas* sp. DS-K-2D1. A seed culture was prepared in the same manner as in Example 1 except that a culture medium containing 1% peptone, 1% yeast extract, and 1% glycerol was used.

Thereafter, 4 minimal culture media were prepared in the same manner as in Example 1 except that 63 g of racemic 3-chloro-1,2-propanediol was used, and the $Ca^{2+}$ concentration of the culture media at the beginning of culturing was adjusted to be 3, 9, 15, or 27 ppm. In the $Ca^{2+}$ concentration of these minimal culture media at the beginning of culturing, 3 ppm was derived from the seed culture.

Each minimal culture medium was combined with 100 ml of the aforementioned seed culture to conduct a reaction (culturing) at 30° C. and 450 rpm with a ventilation volume of 0.25 l/min for 70 hours. The pH was measured and controlled by a pH controller. The pH decrease due to the dechlorination reaction was titrated using a 25% (w/w) aqueous sodium hydroxide solution so as to maintain the pH at 6.9.

Racemic 3-chloro-1,2-propanediol was continuously supplied as in Example 2 in an amount 1.35 times as much as the molar amount of sodium hydroxide added according to the titration. The supply of racemic 3-chloro-1,2-propanediol was terminated when the total amount thereof reached 160 g, except that when the $Ca^{2+}$ concentration at the beginning of culturing was 3 ppm, the total amount of racemic 3-chloro-1,2-propanediol supplied was 139 g. The concentration of racemic 3-chloro-1,2-propanediol during culturing did not exceed 5%, which is the threshold of the growth inhibition concentration of the aforementioned microorganism. The reaction was terminated when the optical purity of the remaining (R)-3-chloro-1,2-propanediol measured by gas chromatographic analysis reached 99.0% e.e. or greater.

Table 4 below shows the relationship between $Ca^{2+}$ concentration and reaction time and between $Ca^{2+}$ concentration and yield. It is clear from Table 4 that when the $Ca^{2+}$ concentration was from 9 to 27 ppm, the optical purity of the remaining (R)-3-chloro-1,2-propanediol exceeded 99% e.e. A $Ca^{2+}$ concentration of 9 ppm resulted in a particularly short reaction time. When the $Ca^{2+}$ concentration was 3 ppm, after 45 hours from the beginning of culturing, the molar ratio of the chlorine ions generated as the substrate was decomposed to the sodium hydroxide necessary for neutralization fluctuated so that the feeding reaction did not progress efficiently. Therefore, the optical purity of the remaining substrate reached 99% e.e. during culturing, resulting in a shortage of the carbon source and the termination of the reaction because the racemic substrate added by feeding could not be optically resolved stably. As a result, only 139 g was utilized in the optical resolution (87% of the initially estimated 160 g). When the molar ratio of the substrate introduced by feeding relative to sodium hydroxide was increased, the concentration of reaction by-product glycidol (T. Suzuki et al., *Appl. Microbiol. Biotechnol.* 1993, 40, 273-278) increased, thereby inhibiting the growth of the microorganism and hence the assimilative optical resolution. Table 4 shows the results of the reaction in relation to $Ca^{2+}$ concentration.

TABLE 4

| $Ca^{2+}$ concentration* (ppm) | Reaction time (hours) | Optical purity (% e.e.) | Yield of R-isomer (>99% e.e.) |
| --- | --- | --- | --- |
| 3 | 45 | >99 | The reaction was terminated before completion. |
| 9 | 41 | >99 | 46.0 |
| 15 | 46 | >99 | 46.7 |
| 27 | 51 | >99 | 47.0 |

The optical purity of (R)-3-chloro-1,2-propanediol in the culture was measured as with the (R)-3-chloro-1,2-propanediol of Example 2.

Example 4

Continuous Culturing

A 500 ml Erlenmeyer flask equipped with baffles and accommodating a 100 ml liquid culture medium containing 10 g/l glycerol, 10 g/l yeast extract and 10 g/l peptone (pH 7.2) was autoclaved at 121° C. for 15 minutes. In this flask was inoculated a small amount of *Pseudomonas* sp. DS-S-RP8 that had been cultured on a culture plate having the same nutrients, and cultured at 30° C. for 24 hours, thereby giving a seed culture.

Ion-exchanged water was used to prepare a 1 l aqueous solution containing inorganic components as shown in Table 1 of 10 ppm using calcium chloride. This aqueous solution was mixed with 40 g of racemic 1,2-propanediol as a sole carbon source, thereby giving a minimal culture medium. This minimal culture medium was accommodated in a 2 l fermentor and steam-sterilized under pressure at 121° C. for 15 minutes. Forty milliliters of the seed culture was introduced thereto to carry out batch culturing at 30° C. and 500 rpm with a ventilation volume of 0.1 l/min for 15 hours. The turbidity created by the microorganism after 15 hours was 8.6 OD (at 660 nm), and the concentration of 1,2-propanediol at that time was 2.2%. The pH was measured and controlled by a pH controller using a 3 N aqueous sodium hydroxide solution to maintain the pH at 6.9.

Continuous culturing was then initiated as follows. A 2 l fermentor containing one liter of the aforementioned aqueous solution of inorganic components having a $Ca^{2+}$ concentration of 10 ppm (pH 6.9) was steam-sterilized under pressure at 121° C. for 15 minutes, and then connected to the first fermentor. Culturing conditions in the first and second fermentors, such as temperature, ventilation volume, pH, and the like, were as in the batch culturing. An aqueous solution the same as the aforementioned aqueous solution of inorganic components having a $Ca^{2+}$ concentration of 10 ppm was mixed with racemic 1,2-propanediol, such that the final concentration of racemic 1,2-propanediol was 100 g/l, as a sole carbon source for use as a culture medium to be supplied during continuous culturing. Continuous culturing was carried out while controlling the culture medium supply rate to maintain the turbidity created by the microorganism in the first fermentor at 11 OD (at 660 nm). As a result, equilibrium was reached with a culture medium supply rate of 0.0159 l/hour. In this instance, the retention time was 126 hours. In the first fermentor, the concentration of 1,2-propanediol was maintained at 6.8%, the specific growth rate μ was maintained at 0.0159 (hour$^{-1}$), and the specific substrate utilization rate v was maintained at 0.048 (g/OD·hour·1). In the second fermentor in this instance, the turbidity created by the microorganism was 14 OD (at 660 nm), and the concentration of 1,2-propanediol was 3.8%. Analysis of the optical purity of 1,2-propanediol contained in the culture fluid discharged from the second fermentor carried out as in Example 1 revealed (R)-1,2-propanediol of 98% e.e. or greater.

What is claimed is:

1. A method for producing an optically active compound comprising:
    a first step of culturing a microorganism belonging to the genus *Pseudomonas* capable of assimilating either the R-isomer or the S-isomer of a compound represented by Formula (1):

(1)

wherein R is a methyl, ethyl, propyl, chloromethyl, or hydroxyethyl group, in a culture medium whose $Ca^{2+}$ concentration at the beginning of culturing is 5 to 40 ppm and which contains a racemic mixture of the compound as a carbon source; and
    a second step of recovering the optically active compound remaining in the culture broth.

2. The production method according to claim 1, wherein the compound represented by Formula (1) is 1,2-propanediol, the $Ca^{2+}$ concentration of the culture medium at the beginning of culturing in the first step is 9 to 13 ppm, and (R)-1,2-propanediol is recovered in the second step.

3. The production method according to claim 2, wherein the microorganism is *Pseudomonas nitroreducens* DS-S-RP8 (International Deposition No. FERM BP-7793).

4. The production method according to claim 1, wherein the compound represented by Formula (1) is 3-chloro-1,2-propanediol, the $Ca^{2+}$ concentration of the culture medium at the beginning of culturing in the first step is 7 to 40 ppm, and (S)-3-chloro-1,2-propanediol is recovered in the second step.

5. The production method according to claim 4, wherein the microorganism is *Pseudomonas* sp. DS-SI-5 (International Deposition No. FERM BP-7080).

6. The production method according to claim 1, wherein the compound represented by Formula (1) is 3-chloro-1,2-propanediol, the $Ca^{2+}$ concentration of the culture medium at the beginning of culturing in the first step is 5 to 28 ppm, and (R)-3-chloro-1,2-propanediol is recovered in the second step.

7. The production method according to claim 6, wherein the microorganism is *Pseudomonas* sp. DS-K-2D1(International Deposition No. FERM BP-3096).

8. The production method according to claim 1, wherein the compound represented by Formula (1) is 1,2-propandiol or 3-chloro-1,2-propanediol.

9. The production method according to claim 1, wherein the microorganism is *Pseudomonas nitroreducens* DS-S-RP8 (International Deposition No. FERM BP-7793), *Pseudomonas* sp. DS-SI-5 (International Deposition No.-7080), or *Pseudomonas* sp. DS-K-2D1(International Deposition No. FERM BP-3096).

10. The production method according to claim 1, wherein the method is carried out using fed-batch culturing or continuous culturing.

* * * * *